(12) United States Patent
Parris

(10) Patent No.: US 12,343,560 B1
(45) Date of Patent: Jul. 1, 2025

(54) DEVICE FOR TRAPPING ABNORMAL MOTILE CELLS

(71) Applicant: George Edward Parris, Gaithersburg, MD (US)

(72) Inventor: George Edward Parris, Gaithersburg, MD (US)

(73) Assignee: DIRECTED ENERGY MATERIALS LLC, Woodbridge, VA (US)

( * ) Notice: Subject to any disclaimer, the term of this patent is extended or adjusted under 35 U.S.C. 154(b) by 0 days.

(21) Appl. No.: 18/915,417

(22) Filed: Oct. 15, 2024

(51) Int. Cl.
*A61N 5/10* (2006.01)
*A61K 38/38* (2006.01)

(52) U.S. Cl.
CPC ............ *A61N 5/1001* (2013.01); *A61K 38/38* (2013.01); *A61N 2005/1087* (2013.01); *A61N 2005/1089* (2013.01)

(58) Field of Classification Search
None
See application file for complete search history.

(56) References Cited

U.S. PATENT DOCUMENTS

| 11,383,093 | B1* | 7/2022 | Lee | A61N 2/002 |
| 2009/0117168 | A1* | 5/2009 | Keenan | A61L 29/00 |
| | | | | 424/423 |
| 2011/0270395 | A1* | 11/2011 | Blackwell | A61F 2/4465 |
| | | | | 600/3 |
| 2015/0290363 | A1* | 10/2015 | Pacetti | A61L 31/16 |
| | | | | 427/2.25 |

* cited by examiner

*Primary Examiner* — Thaddeus B Cox
(74) *Attorney, Agent, or Firm* — Peter R Kramer; Ingenium Patents LLC

(57) ABSTRACT

The present invention discloses a device for trapping abnormal motile cells. The device comprises a biocompatible implant to be placed into a patient's body. The biocompatible implant comprises an attractant layer configured to attract and trap abnormal motile cells. The biocompatible implant further comprises an anti-cancer layer configured to kill the trapped abnormal motile cells. The attractant layer comprises natural chemokines, synthetic drugs, or a naturally occurring compounds that attract abnormal motile cells. The anti-cancer layer comprises a radiation layer, an anti-cancer drug, or an electrically conductive layer.

6 Claims, 5 Drawing Sheets

DEVICE FOR TRAPPING ABNORMAL MOTILE CELLS

TECHNICAL FIELD

The present disclosure relates generally to abnormal motile cells, and more particularly, to a device for trapping abnormal motile cells.

BACKGROUND

Metastasis refers to the spread of cancer cells from a primary tumor to surrounding tissues and to distant organs. It is well known that metastasis greatly increases the lethality of cancer. Metastasis is facilitated by motile cancer cells, which are the fusion of cancer cells with normal motile cells such as leukocytes, lymphocytes, or stem cells. The motile cancer cells could travel through the blood or lymph system, and form a new tumor in other organs or tissues of the body. Further, motile cancer cells have receptors, for example, chemokine receptors that cause the motile cancer cells to migrate to specific tissues that are releasing attractants, for example, chemokine ligands. Further, the motile cells possess the molecular machinery that allows them to penetrate tissues.

The motile cancer cells could move passively with the currents of blood and lymph through the normal vessels. Further, when the motile cancer cells encounter high concentrations of certain attractants, for example, chemokines, they are induced to engage in behaviors that cause them to adhere to the vessel walls and penetrate into the surrounding tissues. Thus, tissues and organs that normally secrete high levels of attractants are the unfortunate homing beacons for the motile cancer cells and thus these remote tissues become the targets of metastasis. Recent wounds and areas of irritation calls leukocytes, lymphocytes and stem cells by excreting attractants are also targets for metastasis.

Alternatively, the motile cells gain access to the blood stream via lymph draining. Lymph draining the tumor passively carries the motile cells and cancer cells into local lymph nodes and the motile cells gain access to the blood stream from the lymph nodes. Thus, metastasis could also occur without breaching the tumor. Thus, intercepting the motile cells in the lymph nodes is a very important strategy for preventing metastasis.

Therefore, there is a need for a device for trapping and killing abnormal motile cells.

SUMMARY OF THE INVENTION

The present invention discloses a device for trapping abnormal motile cells. The device comprises a biocompatible implant to be placed into a patient's body. The biocompatible implant comprises an attractant layer configured to attract and trap abnormal motile cells. The biocompatible implant further comprises an anti-cancer layer configured to kill the trapped abnormal motile cells. The attractant layer comprises one or more attractant agents and the anti-cancer layer comprises one or more anti-cancer agents.

In one embodiment, the biocompatible implant comprises a body having a hollow portion, and at least one orifice formed on a surface of the body. The orifice is fluidly connected to the hollow portion.

In another embodiment, the biocompatible implant is a stent. The stent comprises a cylindrical member having a first open end, a second open end opposite to the first open end, and a hollow portion extending between the first open end and the second open end.

In one embodiment, the attractant layer is formed onto at least a portion of the hollow portion. In one embodiment, the anti-cancer layer is formed onto at least a portion of the hollow portion.

In one embodiment, the anti-cancer layer comprises a radiation layer comprising an alpha emitting radionucleotide source. In another embodiment, the anti-cancer layer comprises a radiation layer comprising a beta emitting radionucleotide source. In yet another embodiment, the anti-cancer layer comprises a radiation layer comprising an alpha emitting radionucleotide source and beta emitting radionucleotide source. In yet another embodiment, the anti-cancer agent comprises at least one anti-cancer drug.

In yet another embodiment, the anti-cancer layer comprises an electrically conductive layer. The device is configured to increase the temperature of the electrically conductive layer to a predefined temperature to kill the motile cancer cells. The electrically conductive layer is insulated from a tissue proximal to the biocompatible implant. In one embodiment, the temperature of the electrically conductive layer is increased using electrical induction. In another embodiment, the temperature of the electrically conductive layer is increased by establishing a wired connection to the electrically conductive layer.

In one embodiment, the attractant agents comprise at least one of natural chemokines, synthetic drugs and a naturally occurring compounds that attract the motile cancer cells. In another embodiment, biocompatible implant comprises an adherent layer. The adherent layer comprises a layer of plastic material coated with albumin.

DETAILED DESCRIPTION OF EXAMPLE EMBODIMENTS

Example embodiments of the disclosure now will be described more fully hereinafter with reference to the accompanying drawings, in which example embodiments are shown. The concepts discussed herein may, however, be embodied in many different forms and should not be construed as limited to the example embodiments set forth herein; rather, these embodiments are provided so that this disclosure will be thorough and complete, and will fully convey the scope to those of ordinary skill in the art. Like numbers refer to like elements but not necessarily the same or identical elements throughout.

Definitions

The term "attractant agents" refers to natural chemokines, synthetic drugs or naturally occurring compounds that attract motile cancer cells or that cause the motile cancer cells to accumulate in a tissue.

The term "anti-cancer agents" refers one or more bioactive agents that could kill or inhibit the growth of cancer cells. This includes proteins, peptides, DNA molecules, and hormones, which could be incorporated into the implant to increase the delivery efficacy and treat cancer. The anti-cancer agents further include a chemical agent of synthetic or biological origin that is normally used to treat cancer.

The term "desired release profile" means that the release profile could be tailored by controlling the concentration of the anti-cancer agents and attractants, the microstructure, and the morphology of the implant.

The term "adherent layer" refers to identify surface to coating to which motile cancer cells are inclined to adhere.

Figure 1:
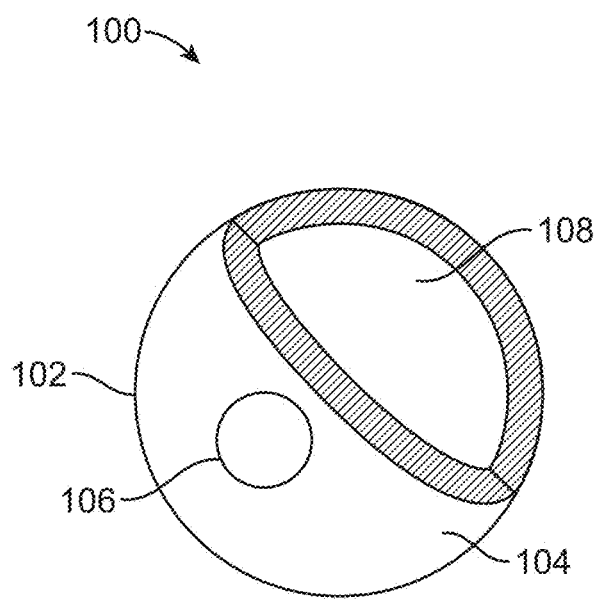
FIG. 1 exemplarily illustrates a device for trapping abnormal motile cells, according to an embodiment of the present invention.
Figure 2:
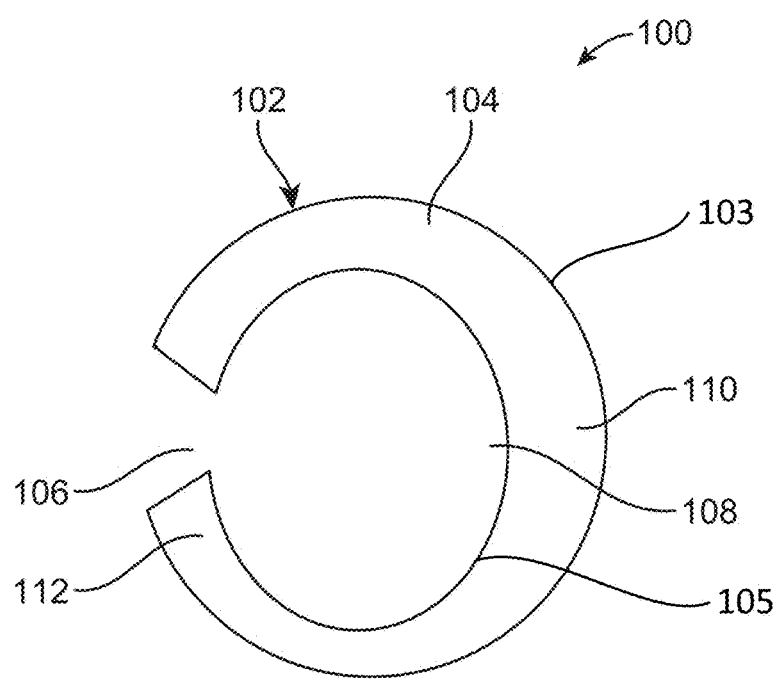
FIG. 2 exemplarily illustrates a cross-section of the device of FIG. 1.
Figure 3:
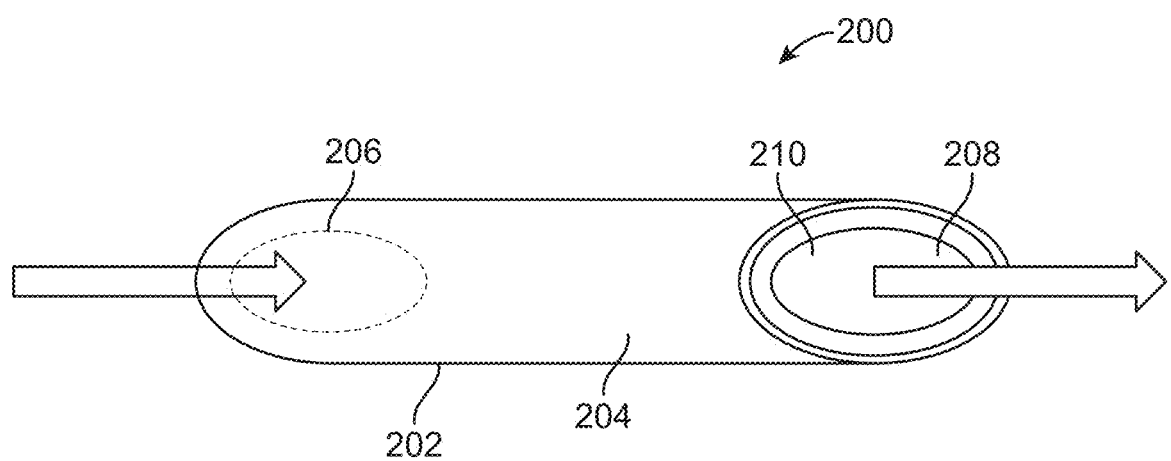
FIG. 3 exemplarily illustrates a device for trapping abnormal motile cells, according to another embodiment of the present invention.

Referring to FIG. 1 to FIG. 3, the device (100, 200) is configured to attract, capture and kill motile cancer cells (also referred as abnormal motile cells) that are likely to facilitate metastasis. Referring to FIG. 1 and FIG. 2, the device 100 comprises a biocompatible implant 102 configured to be placed into a patient's body. The biocompatible implant 102 could be directly implanted into the tumors in the patient's body. Alternatively, the biocompatible implant 102 could be directly implanted at a location proximal to the tumors in the patient's body. The biocompatible implant 102 comprises a body 104 having a hollow portion 108 and at least one orifice 106 formed on a surface of the body 104, an outer surface 103, and an inner surface 105. The orifice 106, is fluidly connected to the hollow portion 108. The hollow portion 108 comprises biocompatible fluid. The hollow portion is substantially bounded by an inner surface 105. The biocompatible fluid, includes, but not limited to, blood plasma and saline.

In one embodiment the device consists of a small hollow implantable envelope or bead of inert material that has at least one opening. Within the hollow interior there are at least two components, a first component for killing or immobilizing cells that enter the envelope through the opening and a second component comprised of a slow-release source of chemokine lure that attracts motile cells.

In one embodiment the implantable envelope or bead contains a slowly diffusing chemotoxic agent that kills cancer cells. The envelope or bead is filled with an adsorbent material that slowly releases a chemokine that attracts motile cells.

In one embodiment, the device is thermally insulated and contains electrically conductive metal fibers or sheets. The metal fibers or sheets are configured to be heated inductively. The device also contains a material that slowly releases a chemokine attractant for motile cells which diffuses from the device through the opening(s). Periodically, the contents of the implanted device are briefly heated to a temperature that is lethal to cells within the device not produce significantly heating outside the device and does not destroy the chemokine attractant. the electrically conductive metal fibers or sheets may be configured as a layer or layers within the hollow portion of the device.

In one embodiment the device contains an alpha or beta emitting radioisotope with the device configured to prevent escape of alpha and beta radiation from the device. For example, radioactive material may be placed such that no direct pathway leads through the opening on the device.

In one embodiment, the device 100 comprises an attractant layer. The attractant layer is formed over at least a portion of the hollow portion 108. The attractant layer comprises one or more attractant agents. The attractant layer is configured to gradually release one or more attractant agents. The attractant agent diffuses from the hollow portion 108 and released through the orifice 106. The attractant agent is configured to attract and trap the motile cancer cells within the biocompatible implant 102. In one embodiment, the attractant layer is a slow-release formulation that attracts leucocytes, lymphocytes and stem cells. The attractant may be a substance embedded in the capsule material which diffuses into the hollow portion 108.

In another embodiment, the device 100 comprises an anti-cancer layer and the attractant layer. The anti-cancer layer is configured to kill the trapped abnormal motile cells. The anti-cancer layer comprises one or more anti-cancer agents. The hollow portion 108 comprises a first portion 112 proximal to the orifice 106, and a second portion 110 that is distal to the first portion 112 and the orifice 106. The anti-cancer layer is formed at the first portion 112 of the hollow portion 108 and the attractant layer is formed at the second portion 110 of the hollow portion 108. The anti-cancer agent may be embedded into an appropriate portion of the capsule material such that it is confined within the device configured so that it does not substantially degrade the attractant or adherent agent.

Referring to FIG. 3, a device 200 comprises a biocompatible implant 202. In one embodiment, the biocompatible implant 202 is a stent. The stent comprises a cylindrical member 204 having a first open end 206, a second open end 208 opposite to the first open end 206 and a hollow portion 210 extending between the first open end 206 and the second open end 208. The stent is adapted to be implanted into the vessels or lymph ducts for draining the tumor. The blood or lymph flows through the hollow portion 210 of the stent via the open ends (206, 208).

The biocompatible implant 202 further comprises an inner layer 212 disposed at the hollow portion 210. The inner layer 212 comprises the attractant layer. In another embodiment, the inner layer 212 comprises the attractant layer and the anti-cancer layer.

The attractant layer is formed over at least a portion of the hollow portion 210. The attractant layer comprises one or more attractant agents. The attractant layer is configured to gradually release one or more attractant agents. The attractant agent is configured to attract and trap the motile cancer cells within the biocompatible implant 202. Referring to FIG. 1 to FIG. 3, in one embodiment, the attractant agent comprises at least one of natural chemokines, synthetic drugs or naturally occurring compounds that attract motile cancer cells or that cause the motile cancer cells to accumulate in a tissue.

The anti-cancer layer is configured to kill the trapped abnormal motile cells. The anti-cancer layer comprises one or more anti-cancer agents. The biocompatible implant 202 is designed to contain anti-cancer agents completely within the hollow portion 210 of the biocompatible implant 202. Further, the stent could be used to protect vulnerable tissues such as bones, which are known to normally release high levels of attractants. Referring to FIG. 1 to FIG. 3, in another embodiment, biocompatible implant (102, 202) further comprises an adherent layer. The adherent layer is coating to which motile cancer cells are inclined to adhere. The adherent layer comprises a layer of plastic material coated with albumin.

Referring to FIG. 1 to FIG. 3, the anti-cancer agent(s) include anti-cancer drugs. The anti-cancer agent(s) further include a chemical agent of synthetic or biological origin. In one embodiment, the anti-cancer agent(s) is comprised of at least one alpha emitting radionuclide and/or at least one beta emitting radionuclide. The radiation source(s) may comprise a layer that is formed over at least a portion of the hollow portion (210, 108). The hollow portion (210, 108) is designed to contain the radioactivity completely within the hollow portion (210, 108) of the biocompatible implant (102, 202).

In another embodiment, an anti-cancer layer comprises an anti-cancer drug. In yet another embodiment, the anti-cancer layer comprises natural toxins that could disable motile cancer cells that enter into the hollow portion (108, 210) of the biocompatible implant (102, 202).

In yet another embodiment, an anti-cancer layer comprises an electrically conductive layer. The device (100, 200) is configured to increase the temperature of the electrically conductive layer to a predefined temperature to kill the motile cancer cells. In one embodiment, the temperature of the electrically conductive layer is increased using electrical induction. In another embodiment, the temperature of the electrically conductive layer is increased by establishing a wired connection to the electrically conductive layer. The electrically conductive layer is insulated from a tissue proximal to the biocompatible implant (102, 202). The electrically conductive layer includes materials from a group including, but not limited to, steel, copper, brass, graphite, gold, silver or aluminum.

In one embodiment, the biocompatible implant (102, 202) is made of plastic material. In another embodiment, the biocompatible implant (102, 202) is made of metallic material. In one embodiment, the biocompatible implant (102, 202) could be used with conventional brachytherapy pellets. The biocompatible implant (102, 202) may be configured to have a desired release profile. Advantageously, the device (100, 200) prevents migration and metastasis of tumor cells by actively attracting and destroying or scavenging motile tumor cells without affecting cells that are not motile or mobile. The device (100, 200) could be safely deployed in the margin of the tumor and nearby healthy tissue, and in appropriate lymph nodes.

Figure 4:
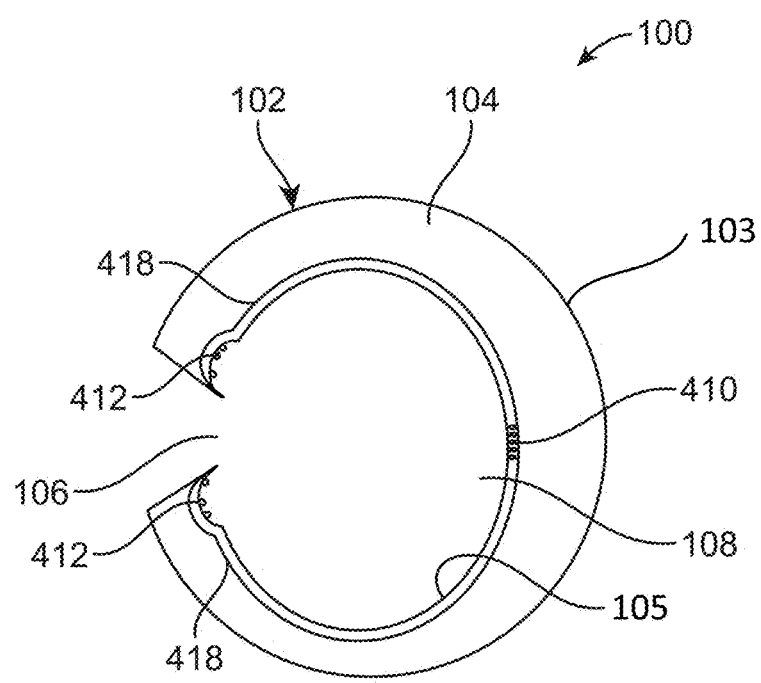
FIG. 4 illustrates an another embodiment of the present invention.

Although the features, functions, components, and parts have been described herein in accordance with the teachings of the present disclosure, the scope of coverage of this patent is not limited thereto. On the contrary, this patent covers all embodiments of the teachings of the disclosure that fairly fall within the scope of permissible equivalents. Although coatings and layers have been explicitly recited, alternative equivalents such as attractant and/or embedded. FIG. 4 illustrates an embodiment with diffusible particles of attractant 410 embedded in the implant body 104 and with non-diffusible particles of killing agent 412, which may be a radioactive substance.

Figure 5:
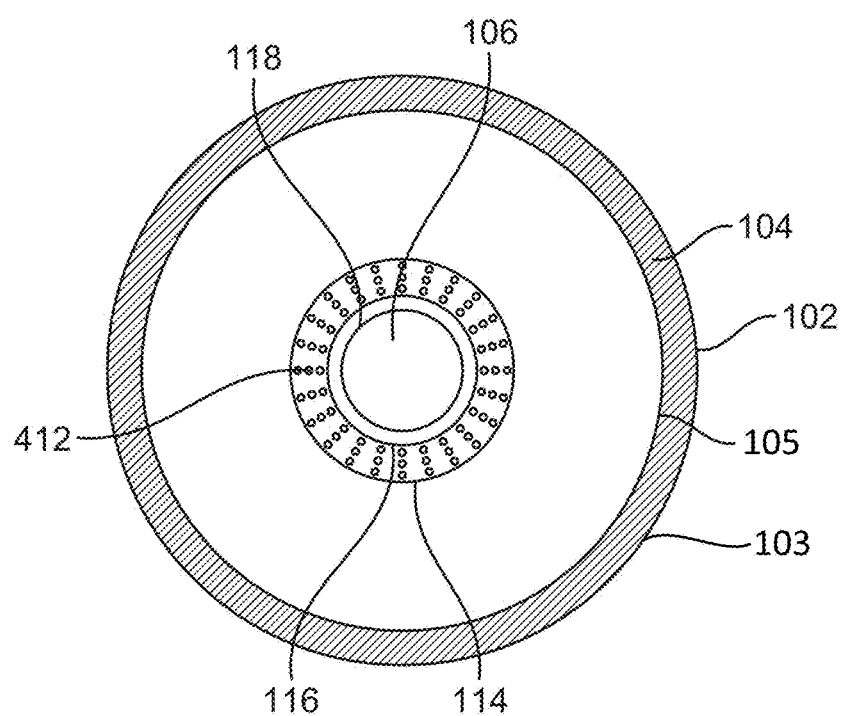
FIG. 5 illustrates the embodiment shown in FIG. 4, showing a cross section as a hemisphere, viewing the inner surface of the device with the orifice at the bottom.

If a radioactive substance is used, the implant includes shielding material 418 to prevent radiation from escaping the implant. If a radioactive substance is used, it is placed in a circular groove having an outer diameter 114 and inner diameter 116 (FIG. 5). The circular groove facing hollow portion such that emitted radioactive particles will impact the inner surface, shielding, and motile cells contained or trapped within the hollow portion, with the radioactive particles being contained by shielding 418, therefore, exposing contents within the hollow portion to radioactive particles. Referring to FIGS. 4 and 5, a radioisotope 412 is positioned in the circular groove such that emitted radioactive particles do not have a straight path to orifice 106, thereby preventing escape of radioactive particles from the device. The recessed groove may be configured with depth and width that focuses the direction of emitted radioactive particles.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense only and not for purposes of limitation.

What is claimed is:

1. A device for trapping abnormal motile cells, comprising:
    a biocompatible implant configured to be placed into a patient's body, the biocompatible implant comprising:
        an outer surface,
        an inner surface,
        a hollow portion,
        an orifice on the outer surface, wherein the orifice is fluidly connected to the hollow portion,
        wherein the inner surface forms a boundary of the hollow portion,
        an anti-cancer layer or zone, wherein said anti-cancer layer or zone is comprised of an alpha and/or beta emitting radionuclide, wherein either the anti-cancer layer is formed on the inner surface at the boundary of the hollow portion, or the radionuclide is embedded into the device to form the anti-cancer zone,
        a shielding material to prevent radiation from escaping from said biocompatible implant, and
        an attractant configured to attract and trap the abnormal motile cells,
        said inner surface and said shielding material forming a recessed circular groove, wherein said alpha and/or beta emitting radionuclide is disposed in the recessed circular groove such that emitted radioactive particles do not have a straight path to the orifice and the emitted radioactive particles are intercepted by the shielding material, thereby preventing escape of the emitted radioactive particles from the device, and further wherein said alpha and/or beta emitting radionuclide is positioned such that the emitted radioactive particles will impact the inner surface, the shielding material, and at least some of the abnormal motile cells contained or trapped within the hollow portion.

2. The device of claim 1, further comprising an adherent layer comprising a layer of plastic material coated with albumin.

3. The device of claim 1, wherein the attractant is comprised of at least one of natural chemokines, synthetic drugs and naturally occurring compounds that attract the abnormal motile cells.

4. The device of claim 1, wherein the recessed circular groove has a depth and width that focuses trajectories of the emitted radioactive particles.

5. The device of claim 1, wherein the recessed circular groove is configured to be concentric with the orifice.

6. The device of claim 1, wherein the outer surface is spherical.

* * * * *